United States Patent [19]

Bess, Jr. et al.

[11] 4,123,982
[45] Nov. 7, 1978

[54] BLIND SUTURING APPARATUS

[76] Inventors: Kenneth B. Bess, Jr., No. 32 Church St., Charleston, S.C. 29401; Benjamin D. Alleman, 17600 NW. 82 Ct., Hialeah, Fla. 33015

[21] Appl. No.: 784,675

[22] Filed: Apr. 5, 1977

[51] Int. Cl.² .............................................. D05B 97/00
[52] U.S. Cl. .................................... 112/169; 112/178
[58] Field of Search ................. 112/169, 80, 176, 178; 128/340

[56]  References Cited
U.S. PATENT DOCUMENTS

| | | | |
|---|---|---|---|
| 2,533,540 | 12/1950 | Warmack | 112/80 |
| 2,601,564 | 6/1952 | Smith | 112/169 X |
| 2,639,683 | 5/1953 | Huntington | 112/169 |
| 2,894,470 | 7/1959 | Buono | 112/169 |
| 2,988,028 | 6/1961 | Alcamo | 112/169 |
| 3,461,827 | 8/1969 | Strobel et al. | 112/178 |
| 4,027,608 | 6/1977 | Arbuckle | 112/169 |

FOREIGN PATENT DOCUMENTS 1,069,457  11/1959  Fed. Rep. of Germany ........... 112/169

Primary Examiner—Werner H. Schroeder
Assistant Examiner—Moshe I. Cohen
Attorney, Agent, or Firm—Clarence A. O'Brien; Harvey B. Jacobson

[57]  ABSTRACT

A hand held and flexible drive shaft powered apparatus is provided for movement along an incision made in flesh or other material and to be sewn closed. The apparatus includes a pair of opposite side drive wheels which are driven from the aforementioned flexible shaft and engage the flesh or other material on opposite sides of the incision therein. The apparatus is driven in a forward direction by the drive wheels along the incision and the forward portion of the apparatus includes a stitching mechanism including an arcuate reciprocally driven needle as well as an oscillatably supported and driven looper whereby a blind suturing operation may be accomplished to close the incision as the apparatus is driven along the incision by the drive wheels.

8 Claims, 15 Drawing Figures

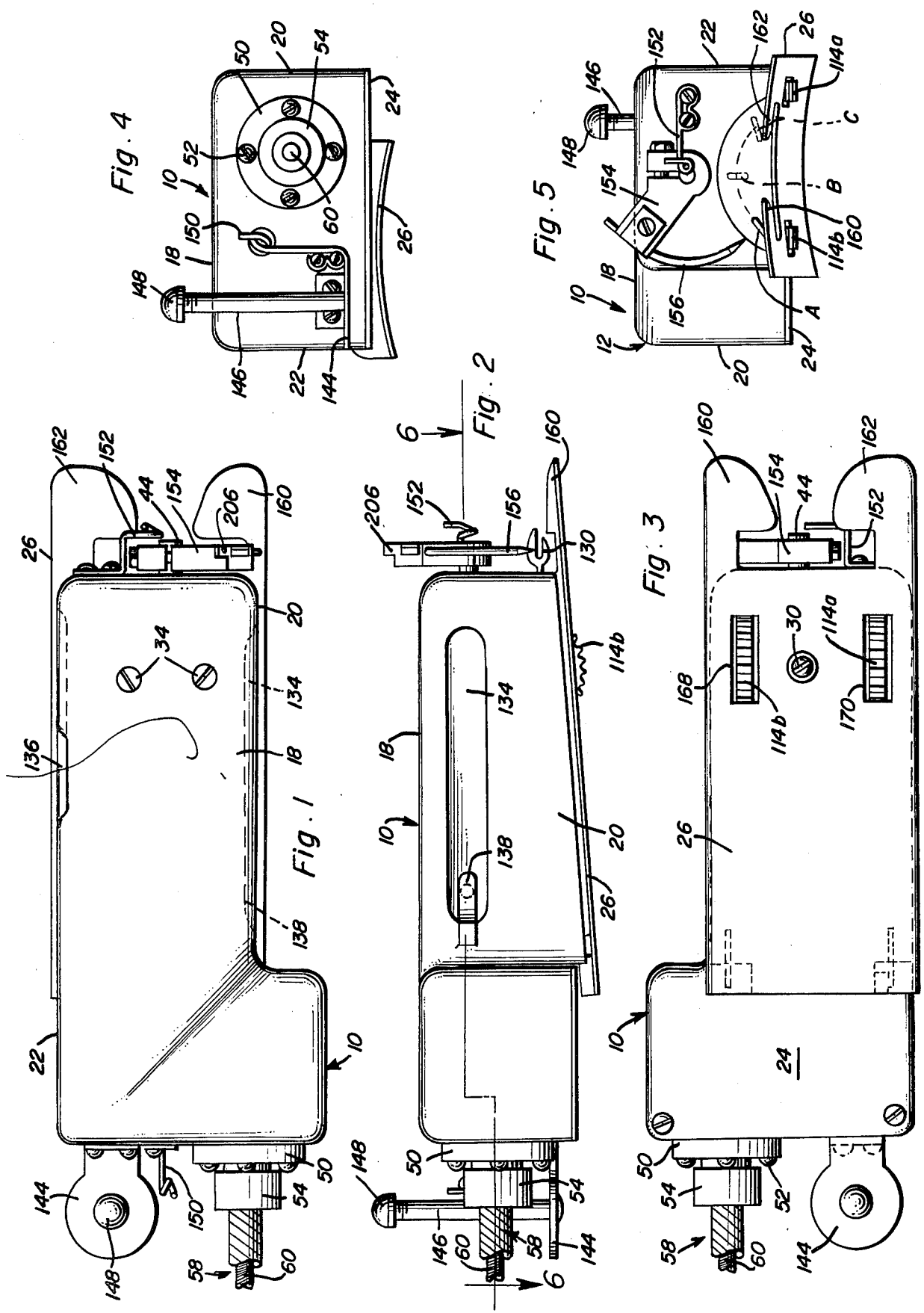

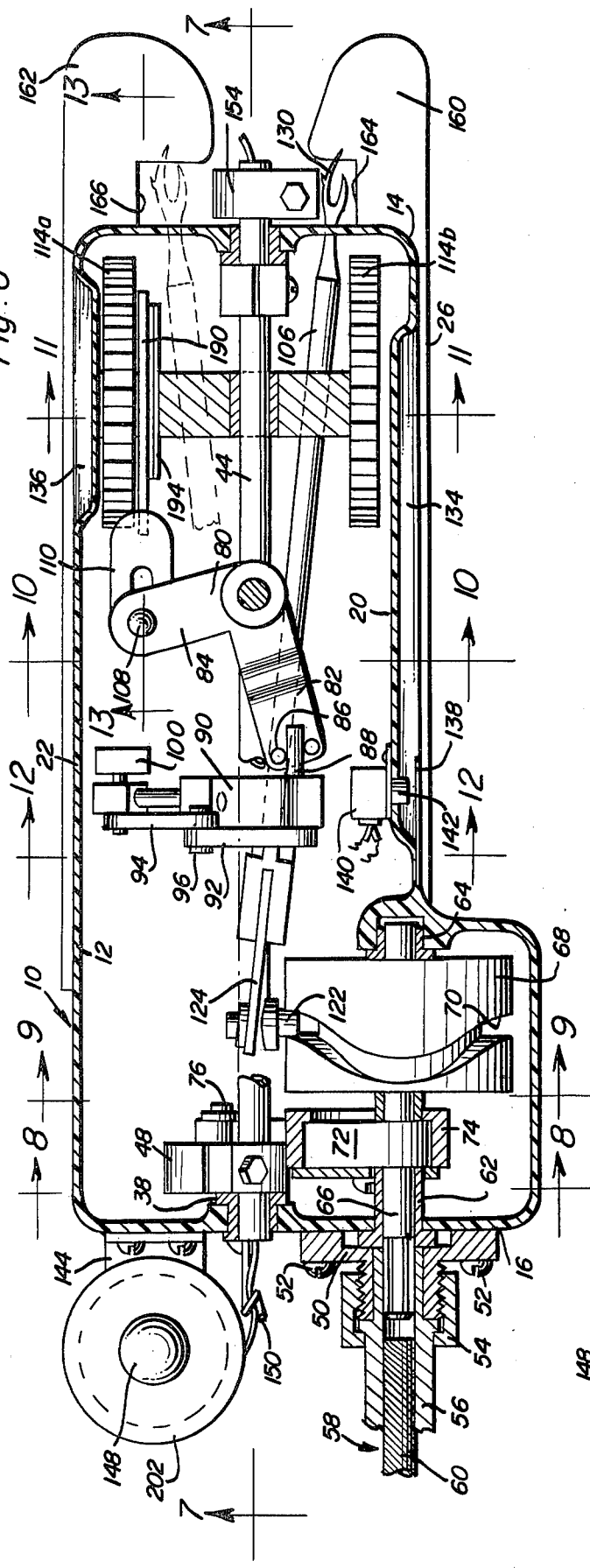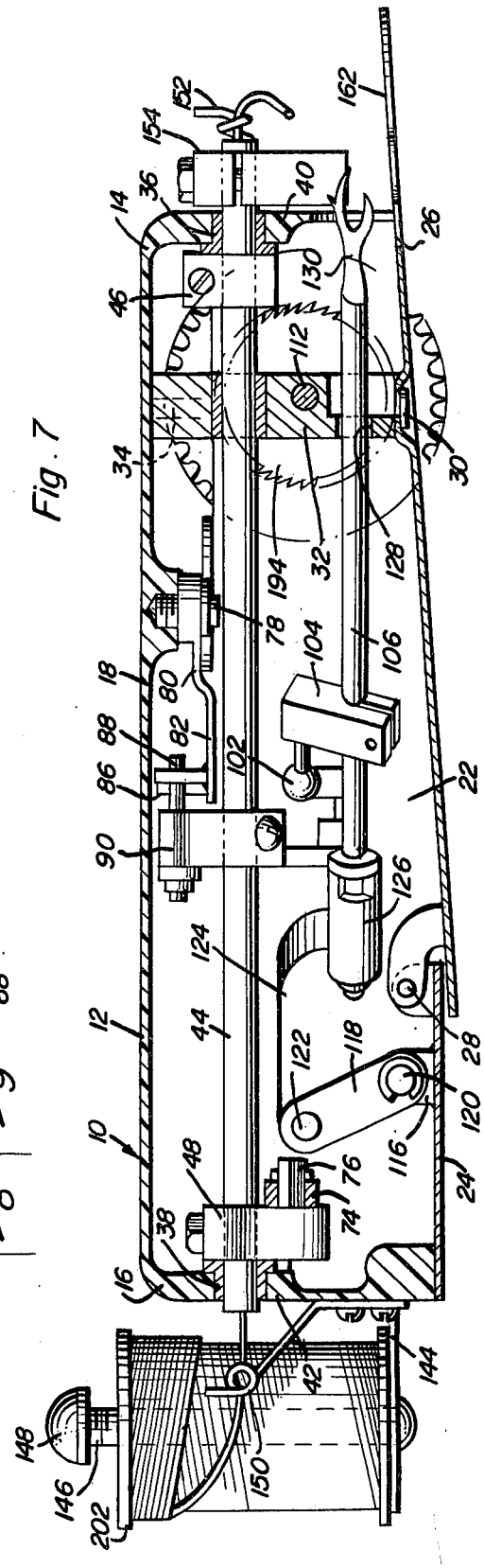

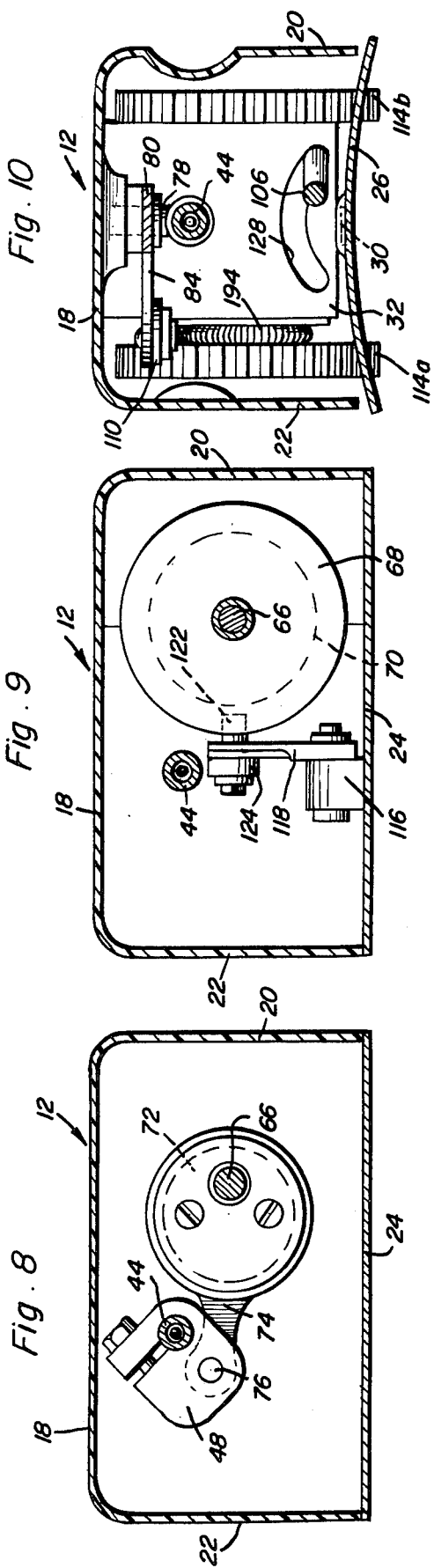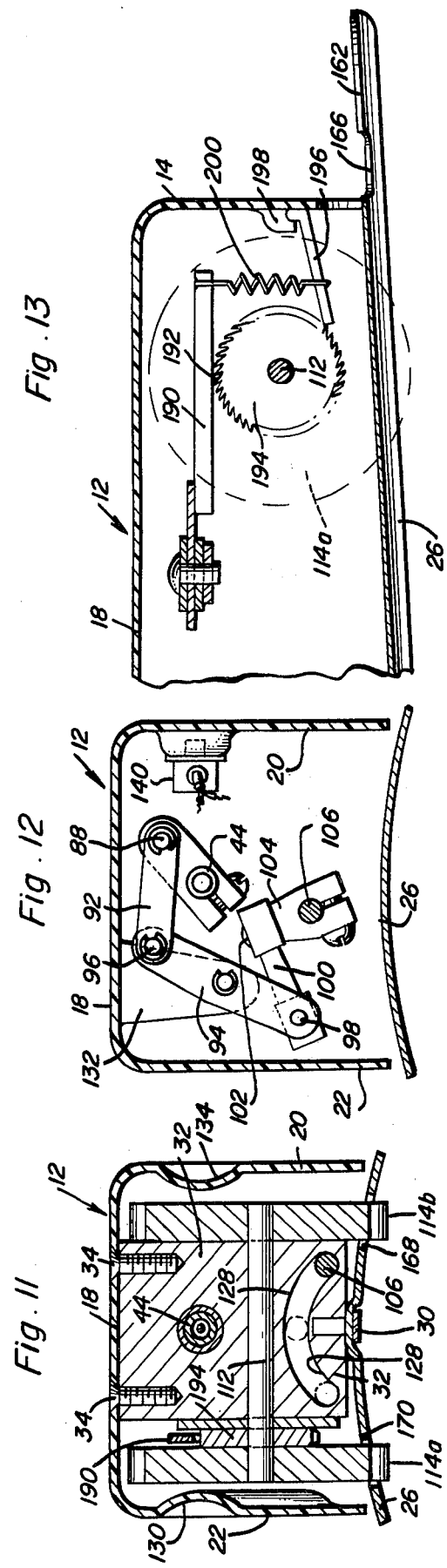

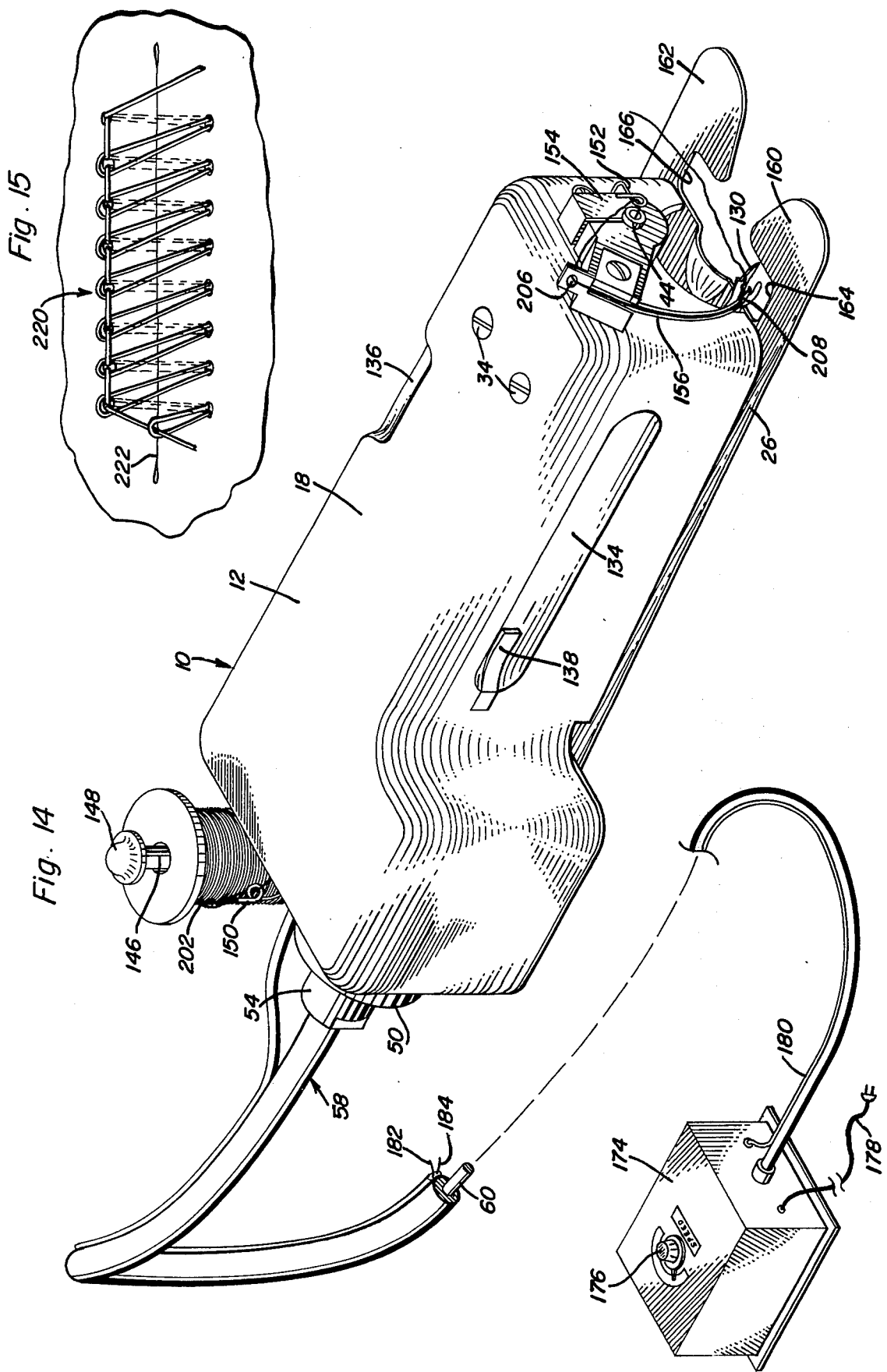

BLIND SUTURING APPARATUS

BACKGROUND OF THE INVENTION

Modern day embalming instruments and techniques are substantially the same as those used in the latter part of the 19th century with a few major changes pertaining primarily to the actual embalming process.

When an individual dies, the medical examination of the body is called an autopsy. In the process of an autopsy, the cavities of the body are opened for the examination by a medical examiner to determine the exact cause of death. The types of autopsies or examinations are: spinal autopsy, thoracic and abdominal autopsy and cranial autopsy. The medical purposes for the autopsy examination are: to determine the cause of death, to determine the manner of death, to determine factors contributing to death, to continue clinical study of death, and to investigate problems of physical an autpmical conditions that are caused by death.

Each of these types of autopsies require incisions which ultimately must be closed by sutures. In addition to autopsied incisions, there are other types of body openings that must be closed with sutures. These openings include gun shot wounds, stabbing wounds, lacerations, punctures, and various others too numerous to mention.

All body openings are presently closed by hand suturing methods and such methods are slow and include certain risk factors.

Probably one of the most hazardous procedures in the embalming process is the suturing of the cadaver. There is always the danger of the person performing the suturing operation being pricked with an infectious needle. There are highly infectious bacteria present in cadavers and the slightest scratch or prick with a suturing needle can cause serious illness, including hepatitis.

The time involved to close a fully posted thoracic, abdominal and crainial autopsied cadaver by hand suturing is generally over 1½ hours. Accordingly, in the interest of safety of the person performing a suturing operation on a cadaver and the saving of time, the development of a motorized blind suturing apparatus for cadavers represents a considerable advance. Still further, hand suturing necessarily results in unevenness in the tightness of successive stitches or sutures and the chance for leakage and seepage is greater than desired.

Examples of various forms of suturing devices, including some of the more general structural and operational features of the present invention are disclosed in U.S. Pat. Nos. 2,580,964, 2,601,564 and 2,988,028.

BRIEF DESCRIPTION OF THE INVENTION

The blind suturing apparatus of the present invention comprises an elongated housing having front and rear ends and the driving end of a flexible drive shaft is removably coupled to the rear end of the housing. The front end of the housing includes underside transversely spaced drive wheels for engaging the tissue of a cadaver on opposite sides of an incision to be closed and a blind suturing mechanism is carried by the front end of the housing, driven by the drive shaft and is operative to form a blind lock stitch for closing the incision along which the housing is advanced by the drive wheels thereof.

The main object of this invention is to provide an apparatus by which incisions may be readily and quickly closed on cadavers.

Another object of this invention is to provide an apparatus capable of performing a blind lock stitch by a blind suturing method.

Still another object of this invention is to provide an apparatus which will be capable of suturing an incision in the tissue of a cadaver with sutures that are of substantially constant tightness and evenness.

Yet another object of this invention is to provide a blind suturing apparatus that may be utilized not only by persons engaged in embalming processes but also by medical examiners, pathologists, veterinarians and taxidermists.

A final object of this invention to be specifically enumerated herein is to provide a blind suturing apparatus in accordance with the preceding objects and which will conform to conventional forms of manufacture, be of simple construction and easy to use, so as to provide a device that will be economically feasible, long lasting and relatively trouble free in operation.

These, together with other objects and advantages which will become subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a top plan view of the apparatus of the instant invention;

FIG. 2 is a side elevational view of the apparatus;

FIG. 3 is a bottom plan view of the apparatus;

FIG. 4 is a rear elevational view of the apparatus;

FIG. 5 is a front elevational view of the apparatus;

FIG. 6 is an enlarged fragmentary horizontal sectional view taken substantially upon the plane indicated by the section line 6—6 of FIG. 2;

FIG. 7 is a longitudinal vertical sectional view taken substantially upon the plane indicated by the section line 7—7 of FIG. 6;

FIG. 8 is a transverse sectional view taken substantially upon the plane indicated by the section line 8—8 of FIG. 6;

FIG. 9 is a transverse sectional view taken substantially upon the plane indicated by the section line 9—9 of FIG. 6;

FIG. 10 is a transverse vertical sectional view taken substantially upon the plane indicated by the section line 10—10 of FIG. 6;

FIG. 11 is a transverse vertical sectional view taken substantially upon the plane indicated by the section line 11—11 of FIG. 6;

FIG. 12 is a transverse sectional view taken substantially upon the plane indicated by the section line 12—12 of FIG. 6;

FIG. 13 is a fragmentary, longitudinal, vertical sectional view taken substantially upon the plane indicated by the section line 13—13 of FIG. 6;

FIG. 14 is a perspective view of the blind suturing apparatus; and

FIG. 15 is a plan view of a portion of a cadaver having an incision therein closed by means of the suturing apparatus of the present invention.

DESCRIPTION OF THE PREFERRED EMBODIMENT

Referring now more specifically to the drawings, the numeral 10 generally designates the blind suturing apparatus of the instant invention. The apparatus 10 includes an elongated housing 12 to be constructed of plastic or other suitable materials and which includes front and rear ends 14 and 16, the housing 12 being provided with a top wall 18 and depending opposite side walls 20 and 22. The housing 12 opens downwardly and the lower portion of the rear end thereof is closed by means of a rear bottom plate 24 from which a bottom support plate 26 substantially fully closing the underside of the forward portion of the housing 12 is pivotally supported as at 28 from the bottom plate 24, the forward end of the support plate 26 being supported by means of an adjusting screw 30 from a feed roller support bracket 32 mounted within the forward portion of the housing 12 by means of suitable fasteners 34.

Front and rear bushings 36 and 38 are secured through the front and rear walls 40 and 42 of the housing 12 and a hollow shaft 44 is journaled from the bushings 36 and 38. A retaining clamp 46 is mounted on the shaft 44 immediately inwardly of the bushing 36 and one end of an arm 48 is mounted on the shaft 44 immediately inwardly of the bushing 38. Further, the rear wall 16 has a flexible shaft mounting fitting 50 secured to the outer side thereof by means of fasteners 52 and the fitting 50 includes a threaded nipple 54 by which the outer housing 56 of a flexible shaft assembly referred to in general by the reference numeral 58 is secured within the fitting 50, the flexible shaft assembly 58 including a rotatable core 60. The fitting 50 supports a bushing 62 secured through the rear wall 16 and a forward portion of the housing 12 supports a further housing 64 in alignment with the bushing 62. A shaft 66 is journaled in the bushings 62 and 64 and the core 60 of the flexible drive shaft 58 is drivingly connected to the shaft 66. The shaft 66 has a cam 68 mounted thereon provided with a peripheral cam groove 70 and the shaft 66 also has an eccentric 72 thereon journaled in one end of a bell crank 74. The other end of the bell crank 74 is oscillatably mounted on a pin 76 carried by the end of the arm 48 remote from the shaft 44.

The central portion of the top wall 18 of the housing 12 supports a pivot pin 78 therefrom and a bell crank 80 is oscillatably supported from the pivot pin 78 and includes first and second arms 82 and 84. The free end of the arm 82 includes a pair of upstanding pegs 86 between which a forward end of a pin 88 is received and the pin 88 is carried by one end of an arm 90 mounted on the midportion of the shaft 44. One end of a connecting link 92 is oscillatably mounted on the pin 88 and the other end of the link 92 is connected to a first end of a pivot arm 94 by means of a pivot connector 96 and the other end of the pivot arm 94 is connected by a pivot pin 98 to one end of a connecting link 100 whose other end is connected by means of a ball joint 102 to a control arm 104 clamped in position on a looper arm 106 to be hereinafter more fully set forth.

The free end of the arm 84 of the bell crank 80 is connected by a pivot pin 108 to the slotted end of a feed roller actuating arm 110.

The feed roller support bracket 32 journals a feed roller shaft 112 therethrough and the opposite ends of the feed roller shaft have toothed feed wheels 114a and 114b mounted thereon for driving the apparatus 10 along an incision to be sutured.

The bottom plate 24 includes an upstanding mount 116 from which the lower end of a cam follower arm 118 is pivotally supported by a pin 120. The upper end of the cam follower arm 118 includes a laterally directed pin 122 slidably received in the cam groove or slot 70 and the upper end of the cam follower arm 118 has a looper arm pivot mount 124 supported therefrom. The looper mount 124 includes a socket portion 126 in which the base end of the looper arm 106 is anchored. The forward end of the looper arm 106 is slidably and reciprocally received through a looper arm guide slot 128 formed in the feed roller support bracket 32 and the forward end of the looper arm 106 includes a looper head 130.

The intermediate portion of the pivot arm 94 is oscillatably supported from a depending bracket 132 supported from the top wall 18 and the opposite side walls 20 and 22 of the housing 12 include finger engageable longitudinally extending and outwardly opening grooves 134 and 136, the groove 134 having a finger engageable spring-type switch actuator 138 operatively associated therewith and the side wall 20 having a switch 140 supported therefrom including an operator 142 engageable by the actuator 138 in order to close the switch 140.

The rear wall 16 of the housing 12 mounts a spool support bracket 144 therefrom including an upstanding spool holder shaft 146 provided with a threadedly mounted spool retaining cap 148 on its upper end. In addition, a rear suture support 150 is supported from the rear wall 16 and a front suture support 152 is supported from the front wall 40.

The forward end of the shaft 44 projects through the front wall 40 and has one end of a needle holder arm 154 supported therefrom and the base end of an arcuate needle 156 is supported from the other end of the needle support arm 154.

The forward end of the support plate 26 defines a pair of forwardly projecting opposite side arms 160 and 162 disposed on opposite sides of a vertical longitudinal plane along which the shaft 44 extends and the arms 160 and 162 are notched as at 164 and 166 in order to define a suturing area through which the needle 156 may swing. In addition, the plate 26 has a pair of opposite side openings 168 and 170 formed therein through which the lower peripheral portions of the feed rollers or wheels 114a and 114b project.

The flexible shaft assembly 58 extends from the rear of the housing 12 to a variable speed electrically actuated motor unit 174 and is driven thereby. The unit 174 includes a speed control 176, an extension cord 178 by which the unit 174 may be electrically connected with any suitable source of electrical energy, and a control wire 180 including a pair of insulated conductors 182 and 184 which are electrically connected to the switch 140. Accordingly, the switch operator 12 controls operations of the unit 174.

It will be noted from FIGS. 10 through 13 that the plate 26 is transversely arcuate so as to be downwardly concave. In this manner, the underside of the support plate 26 will conform to the generally convex configuration of the surface of a cadaver along which an incision has been made. Further, from FIG. 13 of the drawings it may be seen that the feed roller actuating arm 110 includes a narrow portion 190 equipped with a single depending tooth 192 and that the wheel 114 has a toothed wheel 194 supported from the inner side thereof, the tooth 192 being engageable with the toothed outer periphery of the wheel 194. In addition, a ratchet arm 196 has one end thereof oscillatably supported from the front wall 40 of the housing 12 as at 198 and the other end of the arm 196 is also engaged with the toothed periphery of the wheel 194, an expansion spring 200 being connected between the ends of the arms 190 and 196 engaged with the toothed wheel 194. The arm 196 is provided to prevent reverse rotation of the wheel 194 and front to rear reciprocation of the arm 190 will enable the tooth 192 to advance the wheel 194, and thus the wheels 114a and 114b, incrementally.

A spool 202 of suture material is supported from the spool holder shaft 146 in the manner illustrated in FIG. 14 of the drawings and the suture material is fed through the eye portion of the rear suture support 150. The suture material then extends forwardly through the shaft 44 and passes through the front suture support 152 at the front of the housing 12. The suture material then passes through the hole 206 formed in the needle holder arm and passes down the outer or convex side of the needle 156 which is grooved to receive the suture material. When the suture material reaches the free end of the needle 156, it passes up through the eye 208 formed in the needle 156.

When the switch 140 is closed, the core 60 of the flexible shaft assembly 58 is rotated and the shaft 66 is in turn rotated. Rotation of the shaft 66, of course, causes rotation of the cam 68 and also oscillation of the shaft 44 as well as oscillation of the bell crank 80. Oscillation of the bell crank 80 advances the rollers or wheels 114a and 114b incrementally while oscillation of the shaft 44 causes the needle to be oscillated through an arc of substantially 90°. Also, rotation of the cam 68 causes the looper arm 18 to be shifted back and forth in the housing 12 as well as to be oscillated back and forth between the ends of the slot 128. The looper head 130 has three separate motions. One motion is a back and forth motion, a second motion is its oscillation from side to side in the slot 128 and the third motion is an oscillating motion whereby the looper 118 is oscillated about its longitudinal axis. Thus, the looper head is shifted between the three positions A, B and C, illustrated in FIG 5.

The looper arm 106 moves forward at the extreme left side of the travel and catches the suture from the point of the needle 156, then turns 30°, rises in the slot 128 and travels to the right side of the slot where it shifts back in front of the needle letting the needle pass through the loop in the looper head 130 to secure and complete the stitch. The looper arm then shifts rearward, turns 30° in the opposite direction about its longitudinal axis and swings back through the slot 128 to the opposite side so as to assume the position of picking up another suture stitch from the end of the needle 156. The slot in the feed roller actuating arm 110 is long enough so that only the very last portion of the movement will advance the feed rollers or wheels 114a and 114b. Accordingly, the feed rollers or wheels 114a and 114b will move the machine forward to start the next stitch only when the needle is out of the cadaver and the machine will be at rest before the needle starts back into the cadaver.

At the completion of suturing operation, a blind lock stitch suturing, such as that referred to in general by the reference numeral 220 and illustrated in FIG. 15, is formed. Each of the sutures or stitches will have substantially the same tension and the opposite sides of the incision 222 closed by the suturing 220 will be evenly drawn toward each other.

While the apparatus 10 has been specifically illustrated and described as being designed to effect suturing of autopsied incisions, the apparatus 10 may be used in various stitching operations wherein juxtapositioned marginal edges of panel members are to be sewn together.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A hand supportable and manipulatable blind suturing apparatus including a housing having front and rear extremities, defining a front to rear extending vertical reference plane and adapted to be moved forwardly along juxtaposed marginal edge portions to be sewn together, said housing including a lower side to be disposed over and astraddle said edge portions, an arcuate needle, first means supporting said needle from said housing and forwardly of said front extremity for oscillation in a transverse plane about a front to rear extending axis generally paralleling said plane and generally coinciding with the center of curvature of said needle, said needle being shiftable, upon its oscillation, between a first retracted limit position with the pointed end of said needle disposed to one side of said plane and above said lower side and a second extended limit position with said pointed end advanced downwardly below said lower side, inwardly toward and through said plane and thereafter outwardly from the other side of said plane and upwardly to said second limit position elevated above said bottom side, a looper structure, second means supporting said looper structure from said housing for oscillation back and forth along a path extending through said vertical plane and above said lower side for coaction with said needle in its limit positions of movement, and drive means carried by said housing for frictional engagement with material upon which said bottom side is engaged and operative to forwardly advance said housing therealong, and driving means operatively connected to said needle, looper structure and drive means for synchronous driving thereof, said drive means including a pair of toothed wheels journaled from said housing on opposite sides of said vertical plane and for rotation about an axis generally normal to said vertical plane, said wheels including lower peripheral portions projecting slightly below said lower side and disposed rearwardly of said transverse plane, said first means including a main shaft extending lengthwise through said housing, journaled from said housing for oscillation about its longitudinal axis and having said arcuate needle mounted on its forward end, the rear portion of said housing including suture supply support means, said main shaft defining a longitudinal passage therethrough for receiving suture material from said suture supply support means and guidingly supporting suture material extending therethrough to the front portion of said housing.

2. The combination of claim 1 wherein said driving means includes a driven shaft journaled from the rear of said housing, a remote motor and a flexible drive shaft driven from said motor at one end and drivingly connected to said driven shaft at its other end, said driven shaft being drivingly connected to said main shaft, looper structure and drive means.

3. The combination of claim 2 including an operation controlling control for said motor carried by said housing and operable from the latter to selectively actuate and deactivate said motor.

4. The combinaton of claim 2 wherein said looper structure includes a looper shaft extending longitudinally of said housing and having a looper head mounted on its forward end, said looper shaft being supported within said housing for longitudinal shifting relative to said housing, lateral shifting of the front end of said looper shaft transversely of said housing and oscillation of said looper shaft about its longitudinal axis, said second means including means drivingly connecting said driven shaft to said looper shaft for longitudinal shifting in relation to said housing in response to rotation of said driven shaft and means connected between said housing and said looper shaft for oscillation of the latter about its longitudinal axis and lateral back and forth shifting of the front end thereof relative to said housing in response to longitudinal shifting of said looper shaft.

5. The combination of claim 4 including an operation controlling control for said motor carried by said housing and operable from the latter to selectively actuate and deactivate said motor.

6. The combination of claim 1 wherein said drive means includes means for incrementally advancing said wheels only when said needle is in said first retracted position.

7. The combination of claim 1 wherein said needle is transversely flattened in a direction extending along radii of its curvature and includes a longitudinal thread receiving groove formed in and extending along its convex side.

8. The combination of claim 1 wherein the forward portion of said housing includes a base plate portion on its under side whose undersurface defines said plane, and means operatively connected beteen said housing and base plate portion for adjustably shifting the latter relative to the former generally along a path normal to said plane and extending radially of said axis, said apparatus, for the lower peripheral portions of said wheels, being free of portions disposed below or projecting below at least the forward end of said base plate portion.

* * * * *